United States Patent [19]

Knauf

[11] Patent Number: 4,584,278

[45] Date of Patent: Apr. 22, 1986

[54] ANTIGEN DERIVED FROM HUMAN OVARIAN TUMORS AND RADIOIMMUNOASSAY USING THE ANTIGEN

[75] Inventor: Suzanne Knauf, Fairport, N.Y.

[73] Assignee: University of Rochester, Rochester, N.Y.

[21] Appl. No.: 461,770

[22] Filed: Jan. 28, 1983

Related U.S. Application Data

[63] Continuation-in-part of Ser. No. 360,023, Mar. 19, 1982, abandoned.

[51] Int. Cl.$^4$ ............................................. G01N 33/56
[52] U.S. Cl. ..................................... 436/542; 424/1.1; 436/516; 436/536; 436/537; 436/539; 436/543; 436/547; 436/804; 436/813; 436/815; 436/825; 436/828
[58] Field of Search ................................. 436/514–516, 436/536–547, 64, 63, 804, 813, 815, 825, 828; 435/4, 7; 424/1.1; 260/112 R

[56] References Cited

PUBLICATIONS

Hollinshead, A., Devel. Cancer Research, vol. 1, 543–551 (1979).
Stolbach, L. et al., Devel. Cancer Research, vol. 1, pp. 553–557 (1979).
Bhattacharya, M., Barlow, J. J.; Tumor-Associated Antigen for Cystadenocarcinomas of the Ovary, Nat'l Cancer Inst. Monogr., 42:25–32, 1975.
Bhattacharya, M., Barlow, J. J.; Ovarian Tumor Antigens, Cancer (Phila) 42:1616–1620, 1978.
Bhattacharya, M., Barlow, J. J.; Tumor Markers for Ovarian Cancer, Adv. Surg. Oncol., 2:155–176, 1979.
Burton, R. M., Thermostable Antigens (TA) in Ovarian Cancer, Dev. Cancer Res., 1:541–542, 1979.
Burton, R. M., Hope, N. J., Lubbers, L. M.; A Thermostable Antigen of Human Ovarian Cancer, Fed. Proc., 341:1036, 1975.
Burton, R. M., Hope, N. J., Lubbers, L. M.; A Thermostable Antigen Associated with Ovarian Cancer, Am. J. Obstet. Gynecol., 125:472–477, 1976.
Imamura, N., Takahashi, T., Lloyd, K. O., Lewis, Jr. J. L., Old, L. J.: Analysis of Human Ovarian Tumor Antigens Using Heterologous Antisera: Detection of New Antigenic Systems, Int. J. Cancer, 21:570–577, 1978.
Lloyd, K. O.; Ovarian Cancer Antigen, OVC-2, Dev. Cancer Res., 1:533, 1979.
Lloyd, K. O.; Ovarian Cancer Antigen, OVC-1, Dev. Cancer Res., 1:535, 1979.
Knauf, S., Urbach, G. I.; Purification of Human Ovarian Tumor-Associated Antigen and Demonstration of Circulating Tumor Antigen in Patients with Advanced Ovarian Malignancy, Am. J. Obstet. Gynecol., 127:705–710, 1977.
Knauf, S., Urbach, G. I.; The Development of a Double-Antibody Radioimmunoassay for Detecting Ovarian Tumor-Associated Antigen Fraction OCA in Plasma, Am. J. Obstet. Gynecol., 131:780–787, 1978.
Knauf, S., Urbach, G. I.; Identification, Purification, and Radioimmunoassay of NB/70K, A Human Ovarian Tumor-Associated Antigen, Cancer Res., 41:1351–1357, 1981.

Primary Examiner—Thomas G. Wiseman
Assistant Examiner—M. Moskowitz
Attorney, Agent, or Firm—Robert Hallenbeck; Martin LuKacher

[57] ABSTRACT

Methods for the isolation and purification of an antigen, named NB/70K, from human ovarian carcinomas and radioimmunoassays for the detection of ovarian carcinomas, as well as an antibody specific for NB/70K.

18 Claims, 8 Drawing Figures

ANTIGEN DERIVED FROM HUMAN OVARIAN TUMORS AND RADIOIMMUNOASSAY USING THE ANTIGEN

This application is a continuation in part of my application Ser. No. 360,023 filed Mar. 19, 1982, now abandoned.

DESCRIPTION

The present invention relates to the methods for the isolation and purification of both an antigen, which I named NB/70K, and for the antibody to that antigen, namely anti-NB/70K; the antigen and the antibody themselves; and radioimmunoassays which detect the presence of ovarian carcinomas, and particularly to an improved radioimmunoassay which I named the Triton NB/70K assay, which allows for detection of NB/70K in serum samples taken from patients with ovarian carcinomas.

NB/70K is a unique fraction isolated from ovarian tumor homogenates. It is specific for ovarian carcinomas. NB/70K is useful in preparing anti-NB/70K which is required for the radioimunoassay. The assay itself can serve as a diagnostic tool in the detection and monitoring of ovarian carcinomas.

Previously published studies in this field of gynecologic oncolony are set forth below. These studies are numbered and will be referred to by number.

1. Bhattacharya M, Barlow JJ, Tumor-associated antigen for cystadenocarcinomas of the ovary. Nat'l Cancer Inst. Monogr. 42:25–32, 1975.
2. Bhattacharya M, Barlow JJ; Ovarian tumor antigens. Cancer (Phila) 42:1616–1620, 1978.
3. Bhattacharya M, Barlow JJ; Tumor markers for ovarian cancer. Adv. Surg. Oncol. 2:155–176, 1979.
4. Burton RM; Thermostable antigen (TA) in ovarian cancer. Dev. Cancer Res. 1:541–542, 1979.
5. Burton RM, Hope NJ, Lubbers LM; A thermostable antigen of human ovarian cancer. Fed. Proc. 341:1036, 1975.
6. Burton RM, Hope NJ, Lubbers LM; A thermostable antigen associated with ovarian cancer. Am. J. Obstet. Gynecol. 125:472–477, 1976.
7. Imamura N, Takahashi T, Lloyd KO, Lewis JL jr; Old LJ; Analysis of human ovarian tumor antigens using heterologous antisera; detection of new antigenic systems. Int. J. Cancer 21:570–577, 1978.
8. Lloyd KO; Ovarian cancer antigen, OvC-2. Dev. Cancer Res. 1:533, 1979.
9. Lloyd KO; Ovarian cancer antigen, OvC-1. Dev. Cancer Res. 1:535, 1979.
10. Knauf S, Urbach GI; Purification of human ovarian tumor-associated antigen and demonstration of circulating tumor antigen in patients with advanced ovarian malignancy. Am. J. Obstet. Gynecol. 127:705–710, 1977.
11. Knauf S, Urbach GI; The development of a double-antibody radioimmunoassay for detecting ovarian tumor-associated antigen Fraction OCA in plasma. Am. J. Obstet. Gynecol. 131:780–787, 1978.

The following paper, numbered 12, contains a description of the materials and methods used in accordance with the invention and described herein.

12. Knauf S, Urbach GI; Identification, purification, and radioimmunoassay of NB/70K, a human ovarian tumor-associated antigen. Cancer Res. 41:1351–1357, 1981.

The features and advantages of the invention as well as the best known mode for practice thereof will become more apparent from a reading of the following detailed description which makes reference to the following drawings.

Figure 6A:
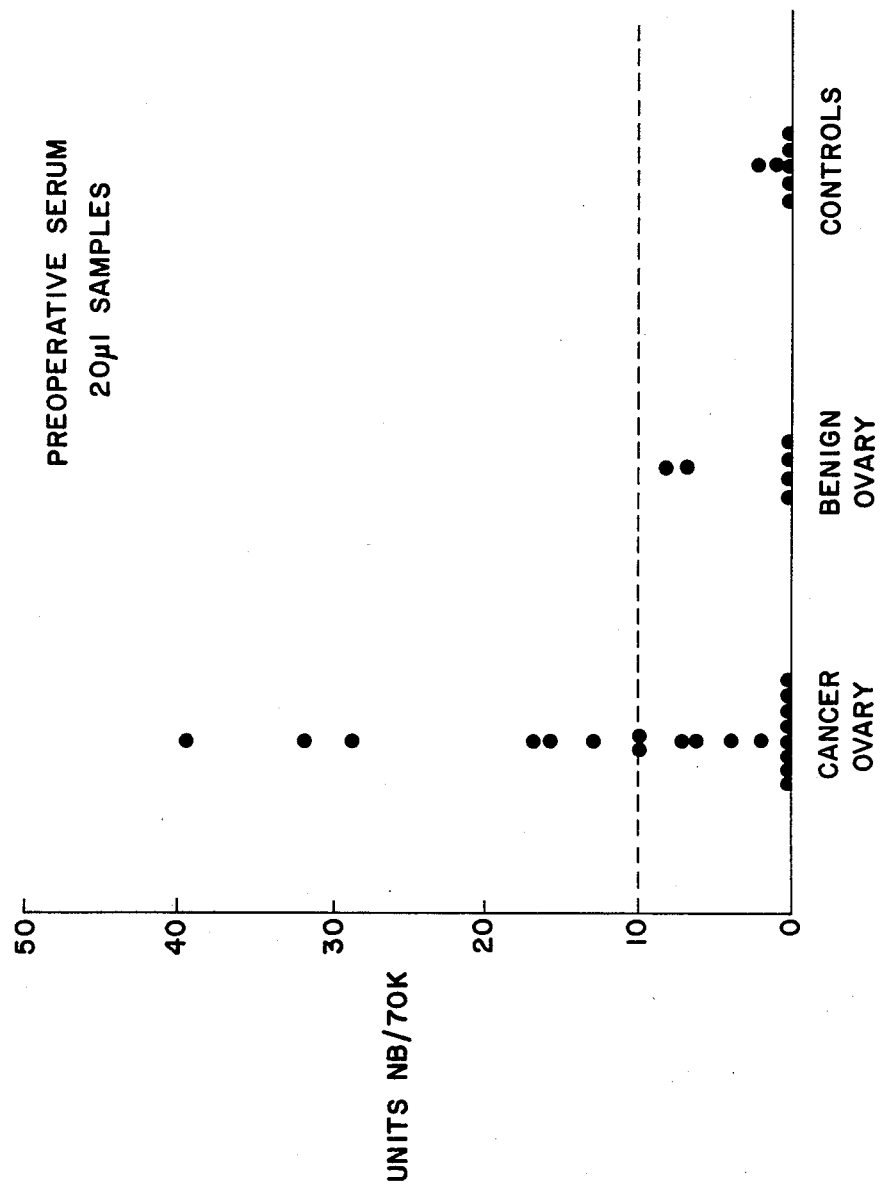
Figure 6B:
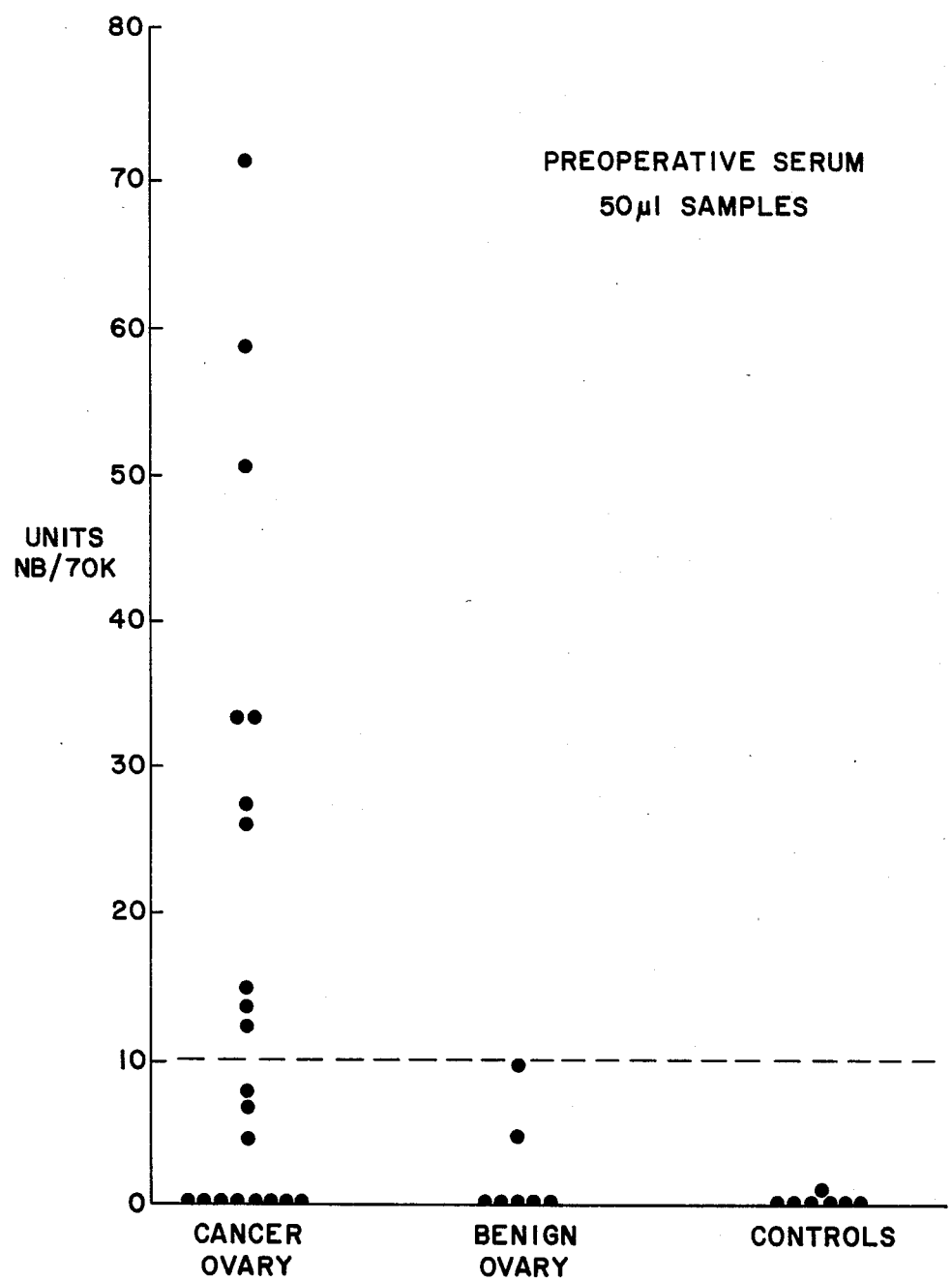

FIG. 6 (a) and (b) are plots showing net NB/70K levels as measured by the Triton NB/70K assay of pretreatment sera from patients with ovarian tumors and controls; FIG. 6(a) NB/70K levels in a 20 ul sample volume, and FIG. 6(b) NB/70K levels in a 50 ul sample volume.

Figure 7:
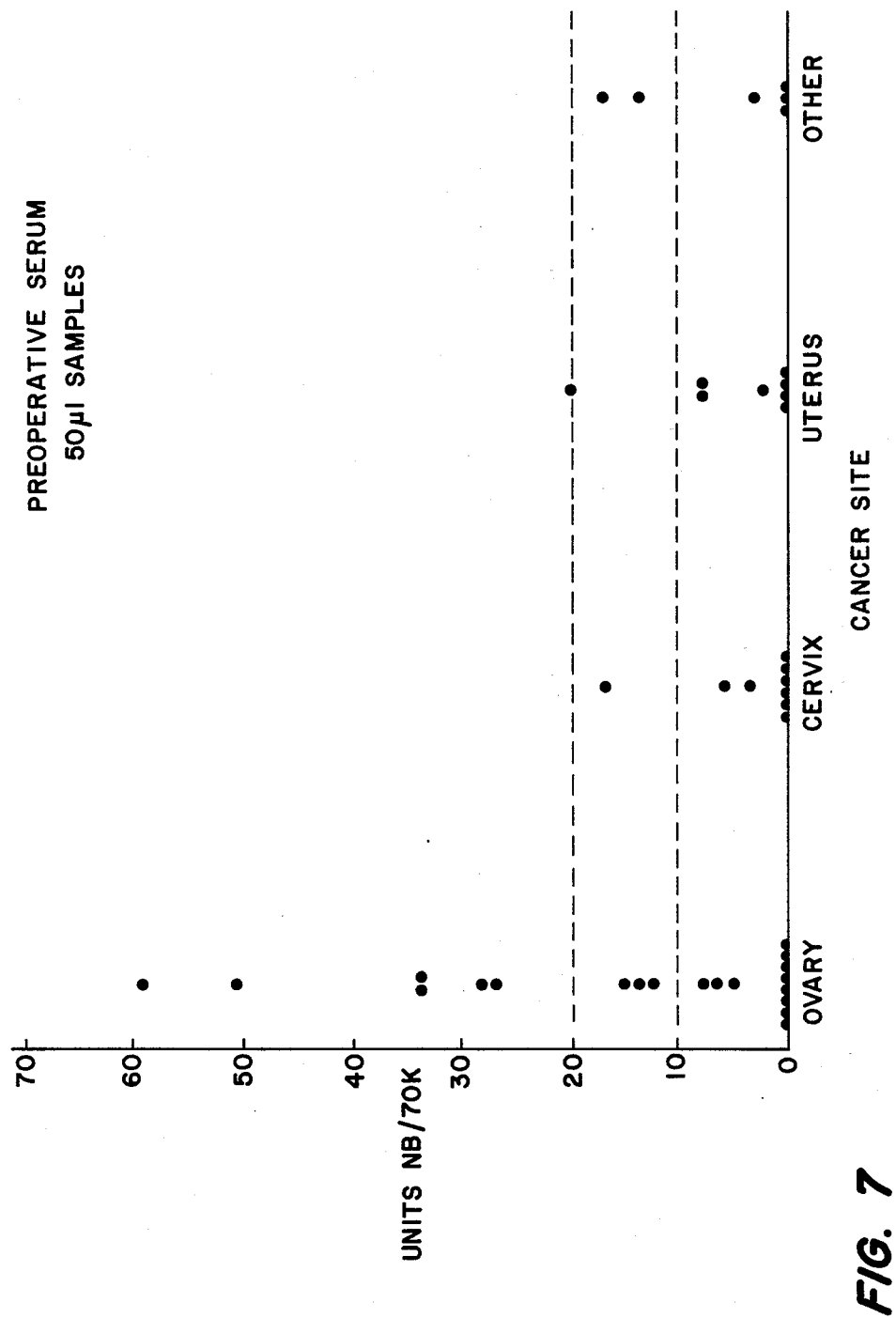

FIG. 7 is a plot showing net NB/70K levels as measured by the Triton NB/70K assay of pretreatment sera from patients with different cancers.

In order to detect ovarian carcinomas, an antigen must be isolated that is specific to the tumor as composed of tumor tissue or cells from which it is isolated. It cannot cross-react with other normal or non-normal tissues. Previous studies have isolated extracts from ovarian carcinomas, denominated OCAA, OCAA-1, OvC-1, OvC-2, but no extract has had the specificity required for diagnostic purposes. (See references 1–9). The difficulties have been in the method of isolation and purification. To insure that an antibody does not cross-react with other than the antigen against which it is directed, the antibody must contain only antibodies directed against tumor-specific antigenic components that have no cross-reactivity with normal or other non-normal components. NB/70K appears to be able to induce antibodies against only tumor-specific components.

Figure 1:
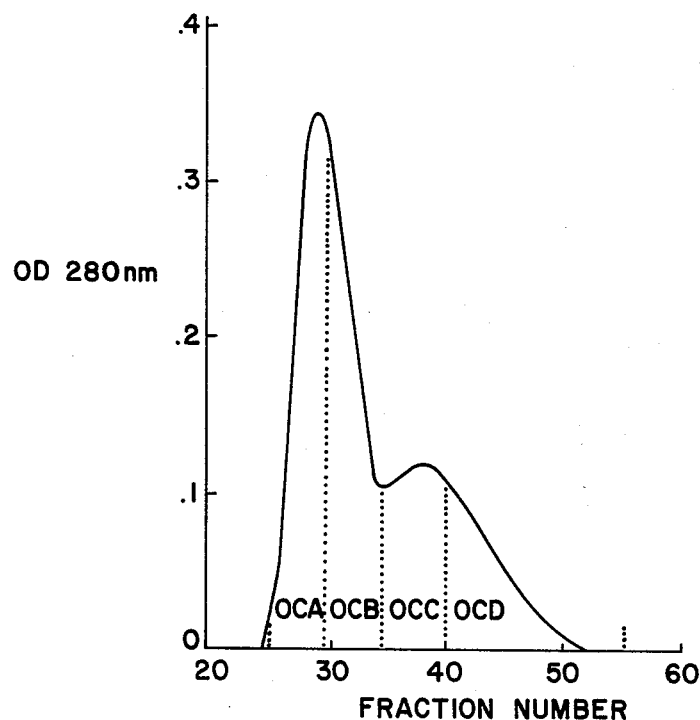
FIG. 1 is a Sephadex G-100 protein elution profile of ovarian antigen.

NB/70K was initially discovered in Fraction OCA. Fraction OCA was prepared from a 10 percent perchloric acid extract of homogenized ovarian tumors. The acid extract was then dialyzed against distilled water and lyophilized. The acid extract was next subjected to affinity chromatography on concanavalin A-Sepharose 4B. Bound protein was eluted with 10 and 25 percent D-mannose. Initial purification of the bound protein containing the antigen in the 10 percent fraction was prepared by passage through a series of affinity columns that contained anti-normal female serum, anti-normal ovarian tissue, and anti-normal serum subfractions coupled to Sepharose 4B. The elutate was concentrated by ultrafiltration. This material in 1 ml of phosphate buffered saline ["PBS" (pH 7.8)] was then chromatographed on Sephadex G-100. One ml fractions, in sequentially pooled drops, were collected therefrom to yield, among others, tumor antigen Fraction OCA. FIG. 1 details the results of this step. An antibody to Fraction OCA was prepared by a modification of Vaitukaitis' method, using female New Zealand white rabbits. 100 ug of protein in 1 ml of Freunds complete adjuvant was injected subcutaneously on days 1, 8, and 60. Gamma globulin was prepared from immune rabbit blood by two precipitations of immune serum with 33 percent saturated ammonium sulfate.

The next step involved the iodination of 2 to 5 ug of Fraction OCA with $I^{125}$ by the chloramine-T method. When Fraction OCA was tested against normal serum components, only 5 percent of the fraction cross-reacts, thus, indicating acceptable specificity. When the antibody, prepared above, was absorbed with normal ovary extracts, only 10 percent of the reactivity of the antibody to Fraction OCA was lost, however, when the antibody was absorbed with extracts of adenocarcinoma of the colon, 90 percent of the reactivity was lost.

Figure 2:
FIG. 2 is an autoradiograph of $I^{125}$ labeled OCA before and after affinity chromatography on antibody 701:Sepharose 4B. Left to right: unbound material (NB/70K), original Fraction OCA, eluted material.

Antibody 701 is a gamma globulin fraction isolated from female New Zealand white rabbits which had been injected with 10% perchloric acid extracts of a precipitate formed between 5 ml of a 1:10 dilution of anti-OCA and 10 mg each of ovarian tissue, normal lung tissue, and adenocarcinoma of the colon extracts. Antibody 701 was covalently coupled to Sepharose 4B. To further purify Fraction OCA, iodinated OCA was run through the antibody 701:Sepharose 4B column, and the unbound material, which contained 40 percent of the initial OCA radioactivity, was electrophoresed on a 5.6% sodium dodecyl sulfate/polyacrylamide gel ("SDS/PAGE"). The resultant antigen NB/70K, is detailed on FIG. 2, where NB/70K appears as a single band with a molecular weight of 70,000 daltons, and is seen migrating just in front of bovine serum albumin. In addition, FIG. 2 shows that, as expected, the colon extracts in PBS. The modified method of Vaitukaitis was again used to generate the gamma globulin fraction containing antibody 701 bound material from the antibody 701:Sepharose 4B column, as expected, does not.

NB/70K can also be prepared from Fraction OCA or OCC by the following method without affecting its activity. Tris buffer, 0.05 M (100 ul), pH 6.8, containing 0.001% Bromphenol blue (hereinafter BPB) and sucrose (0.3 g/ml) was added to 1 ml of Fraction OCA or OCC. The sample was applied to wells preformed in an acrylamide slab (1.5 mm thick) with a 3% stacking gel and a 9% or 6% separating gel which has been prepared without SDS. The samples were electrophoresed until the BPB dye was 1 cm from the end of the slab. The gel was then removed from the sandwich. Horizontal strips 1 cm in height were cut from the gel. Each strip was eluted in 10 ml of PBS at 4° C. After elution for 8 hrs or overnight, the PBS was decanted from the gel. Second and third elutions with additional 10 ml aliquots of PBS were then carried out. The eluted fractions were examined for NB/70K activity using the Triton NB/70K assay. Those fractions with NB/70K were pooled and concentrated.

NB/70K can be iodinated by the chloramine T method, but separation of labelled NB/70K from unbound $I^{125}$ must be accomplished by dialysis against PBS. If the separation is attempted by chromatography on Sephacryl S-200, the $I^{125}$ NB/70K is inactive in the Triton NB/70K assay. The dialysed preparation of $I^{125}$ NB/70K is active in the Triton NB/70K assay.

Once NB/70K was isolated, anti-NB/70K could be prepared in female New Zealand white rabbits as above. Anti-NB/70K is essential in the diagnostic assay of ovarian carcinomas. The below described assays use Fraction OCC as the standard, instead of Fraction OCA. (See FIG. 1). The rationale behind this step is that because NB/70K is a low-molecular weight protein and Fraction OCA is a high-molecular weight fraction, which Fraction OCC is not, Fraction OCC should contain a higher percentage of NB/70K in the total fraction than Fraction OCA. Thus, while NB/70K is a highly specific antigen for human ovarian carcinomas and was isolated from Fraction OCA, it may be isolated from at least two of the fractions in FIG. 1 in identical fashion without altering either the antigen itself or its properties.

To prepare one assay, a standard sample of Fraction OCC with 100 ug of protein per ml, was diluted to a $10^{-3}$ concentration in PBS. The total volume of the dilution was given an arbitrary value of 1000 units of NB/70K activity per ml. From this dilution, 0, 5, 10, 20, 40 or 80 ul of standard were added to 20 ul of a $10^{-3}$ dilution of anti-NB/70K in PBS, for 15 minutes at 37° C.

Figure 3:
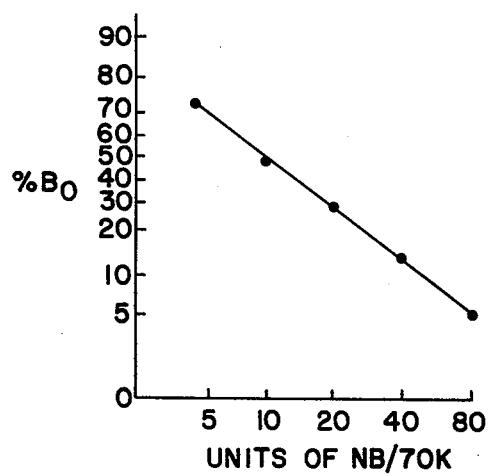
FIG. 3 is a log-logit plot of standard curve data from an assay for NB/70K. $B_0$ is the percentage of maximum binding in the absence of unlabeled antigen. One unit of NB/70K activity equals 1 microliter of a $10^{-3}$ dilution of Fraction OCC.

After this step, iodinated Fraction OCC, prepared similarly to iodinated Fraction OCA to give approximately 35,000 counts per minute in 20 ul of dilution, was added to the reaction mixture, for 1 hour. The solution was next precipitated by the addition of 100 ul of Pansorbin (TM—the generic name is *Staphylococcus aureus* of the Cowan I strain bearing Protein A) (CalBiochem-Behring, LaJolla, Calif.) in an ice water bath, the precipitate was removed by centrifugation, and the radioactivity of the precipitate was counted. The results are detailed in FIG. 3 where it is seen that this assay system achieves a correlation coefficient of 0.98. This means that the percentage of labeled Fraction OCC bound is entirely dependent upon the initial concentration of Fraction OCC.

This assay system has been improved to permit the detection and/or monitoring of the NB/70K content of serum taken from patients suspected to have or being treated for ovarian carcinomas. This improved system of detection and/or monitoring, called the Triton NB/70K assay, provides a reliable tool for the measurement of serum NB/70K levels in ovarian cancer patients.

The Triton NB/70K assay is performed as follows: Fraction OCC or NB/70K was prepared, labeled with $I^{125}$, and diluted in PBS to give 40,000 to 50,000 counts per minute in 20 ul. Fraction OCC or NB/70K was used as the primary standard, where one "unit" of NB/70K activity was arbitrarily set as 0.1 ng of Fraction OCC. Anti-NB/70K was prepared by precipitating out the gamma globulin fraction of serum obtained from female New Zealand white rabbits which had been injected with NB/70K as above. Serum was obtained from blood collected by venipuncture and from out-dated blood blank pools. The blood was allowed to clot a 4° C. and was centrifuged at 1500 g for 10 minutes.

The Triton NB/70K assay used a $10^{-3}$ dilution of Fraction OCC or the appropriate dilution of NB/70K to give 0–150 units of NB/70K activity in a 0–50 ul sample size or a $4 \times 10^{-3}$ dilution of serum to give a 10, 20 or 50 ul sample size. The volumes at each dilution were adjusted to 50 ul with PBS. 20 ul of a 1/60 dilution of gamma globulin from anti-NB/70K in PBS containing 0.01 M EDTA, 0.2% bovin serum albumin and 0.2% Triton X-100, pH 7.5 (hereinafter 0.2% Triton-EDTA buffer) were added to each tube. The test tubes were incubated at 37° C. for 1 hour. 20 ul of iodinated Fraction OCC or NB/70K then were added for an additional hour at 37° C. The tubes were placed in an ice water bath and 100 ul Pansorbin washed twice with PBS and diluted to final concentration of 5% Pansorbin (w/v) in 0.1% Triton-EDTA buffer, was added. After mixing, the tubes were incubated for 1 hour at 4° C. Two ml of cold PBS were added and the tubes were centrifuged at 1500 g for 30 minutes. The supernatants were decanted and the pellets were then counted in a gamma counter.

It is important that Triton-EDTA buffer is used here instead of PBS in the dilution of anti-NB/70K and Pansorbin. The presence of Triton, bovine serum albumin and EDTA in PBS serves to lower the non-specific binding and to increase the binding of Fraction OCC or NB/70K to anti-NB/70K in the assay. The increase in the sample volume from 20 ul to 50 ul allows the range of the standard curve to be increased and the amount of NB/70K measured to also be increased.

Figure 4:
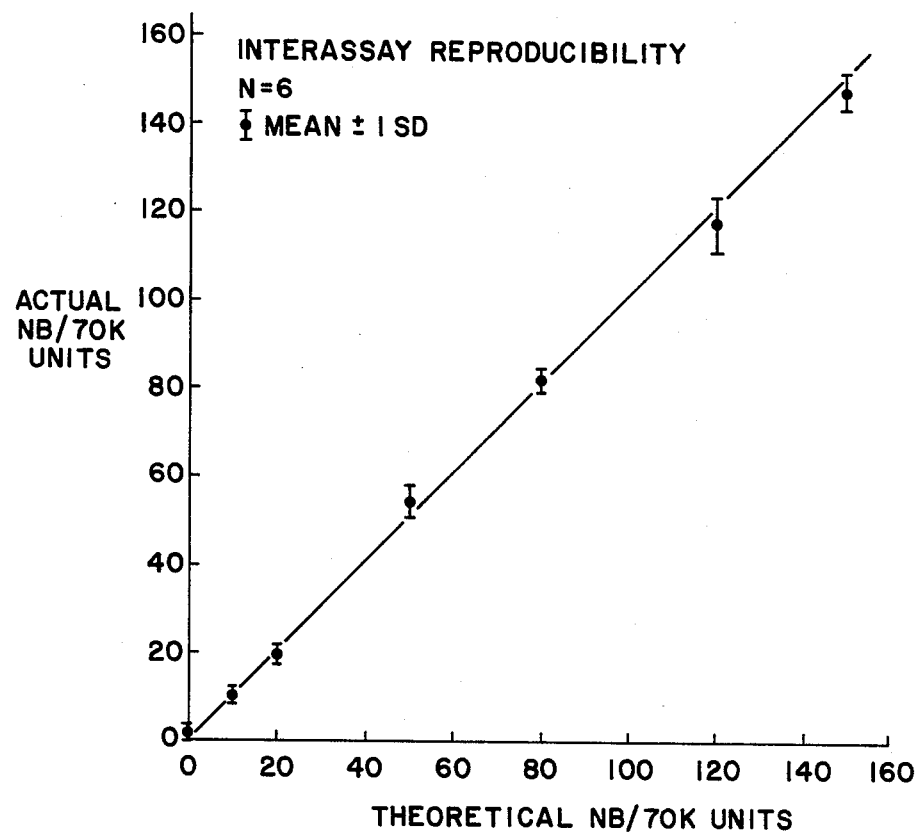
FIG. 4 is a nomogram showing the interassay reproducibility of the Triton NB/70K assay.
Figure 5:
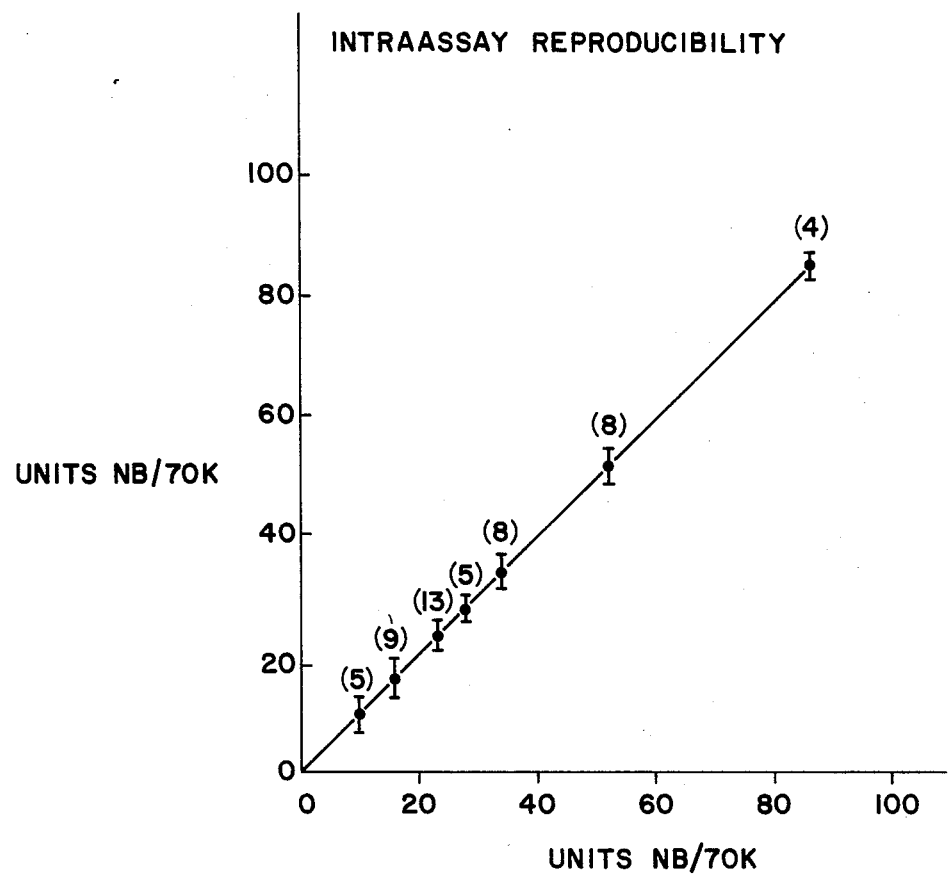
FIG. 5 is a nomogram showing the intraassay reproducibility of the Triton NB/70K assay.

The reliability of this assay is shown in FIG. 4 and FIG. 5, where determinations of specific samples were made either many times on one day (FIG. 4) or over a number of days (FIG. 5). In addition, Tables A and B below show that freezing or refrigerating the serum sample will not adversely affect the reliability of the assay. This will allow the sample to be held over time if the laboratory is busy or if it is to be compared with later samples.

Table A is a table showing the effect of freezing to −70° C. and thawing of serum samples on serum NB/70K levels as measured by the Triton NB/70K assay.

Table B is a table showing the effect of refrigeration of diluted serum samples on NB/70K levels as measured by the Triton NB/70K assay.

TABLE A

Effect of freezing and thawing on serum NB/70K levels as measured by the Triton NB/70K assay

|  | 1X | 2C | 3X |
|---|---|---|---|
| Number of determinations | 15 | 15 | 13 |
| Mean of sample value average sample value | .98 | 1.08 | .93 |
| S.D. of means | .05 | .07 | .07 |

Samples were frozen at −70° C. and thawed before assaying. The sample value obtained after each round of freezing and thawing was divided by the mean of the three values obtained for the sample.
Sample values range from 19 to 60 units of NB/70K activity.

TABLE B

Effect of refrigeration of diluted samples on serum NB/70K levels as measured by the triton NB/70K assay

|  | Day[1] | | |
|---|---|---|---|
|  | 1 | 3 | 7 |
| Number of determinations | 24 | 24 | 24 |
| Mean of sample value average sample value | .97 | 1.02 | 1.00 |
| S.D. of means | .07 | .08 | .07 |

[1]Samples were diluted in PBS on day 1 and then assayed on day 1, day 3 and day 7. Between assays, diluted samples were stored in the refrigerator.

Samples values ranged between 12 and 54 units of NB/70K activity.

Serum samples obtained from patients prior to any treatment were collected and analyzed for NB/70K content. Twenty-one of these patients had ovarian cancer, 7 had benign ovarian cysts or tumors, 9 had cervical cancer, 8 had uterine cancer and 6 had other cancers. Sera from five normal healthy volunteers and 2 patients subsequently found to have no evidence of disease were also analyzed. Net NB/70K levels for 20 ul and 50 ul sample volumes are shown in FIG. 6. Clinical information concerning these patients is presented in Table C.

When serum samples from patients with non-ovarian cancers were examined, only 4 patients had significant (greater than 10 units/50 ul) NB/70K levels (FIG. 7). One patient had an advanced fallopian tube cancer with serous pathology; one had Burkitts Lymphoma; one had a stage IIB squamous carcinoma of the cervix; and one had advanced adenocarcinoma of the endometrium with diffuse peritoneal spread and ascitic fluid positive for malignant cells. These results indicate that NB/70K seem to have specificity for ovarian cancer as compared to non-ovarian malignancies.

TABLE C

Clinical Data of Patients Whose Pretreatment Serum Was Examined in the NB/70K Assay

| PATIENT NO. | Units NB/70K 50 ul | FIGO Stage | Pathological Grade | Pathological Type |
|---|---|---|---|---|
| CA OVARY | | | | |
| 1 | 74 | III | 3 | serous |
| 2 | 59 | III | 2 | serous |
| 3 | 51 | III | 3 | serous |
| 4 | 34 | III | 2 | serous |
| 5 | 34 | IV | 3 | serous |
| 6 | 28 | IV | 2 | serous |
| 7 | 17 | IV | 3 | serous |
| 8 | 15 | IV | 3 | serous |
| 9 | 14 | III | 1 | mucinous |
| 10 | 13 | II | 2 | mucinous |
| 11 | 8 | IV | 3 | serous |
| 12 | 6 | III |  | serous |
| 13 | 5 | I | 1 | mucinous |
| 14 | 0 | III | 2 | serous |
| 15 | 0 | III | 2 | serous |
| 16 | 0 | II |  | granulosa-the |
| 17 | 0 | I | 1 | mucinous |
| 18 | 0 | II | 1 | serous |
| 19 | 0 | III | 3 | undifferentiated carcinoma |
| 20 | 0 | I | 1 | endometroid and mucinous |
| 21 | 0 | III | 1 | serous |

Variations and modifications in the herein described method, antigen, antibody and radioimmunoassays, within the scope of the invention may negate themselves to those skilled in the art. Accordingly, the foregoing descriptions should be taken as illustrative and not in a limiting sense.

I claim:

1. The method of isolation of and purification of an antigen, NB/70K which is specific for ovarian carcinomas, which comprises the steps of incubating an extract of cells, isolated from an ovarian tumor which contain a Fraction OCA, OCB, OCC or OCD, with an antibody which binds to ovarian tissue antigens but does not bind to the ovarian tumor specific antigen NB/70K and separating the unbound, tumor specific antigen NB/70K from the incubation mixture.

2. The method as set forth in claim 1 wherein isolation of said extract of cells comprises the steps of making a perchloric extract of homogenized ovarian carcinoma cells, passing said extract through a concanavalin A:Sepharose 4B column, eluting said extract from said column, passing said eluted extract through a column containing anti-normal female serum, anti-normal ovarian tissue and anti-normal serum subfraction antibodies coupled to Sepharose 4B, passing the unbound extract therefrom through a Sephadex G-100 column and collecting the extract therefrom in 1 ml amounts as sequentially pooled drops.

3. The method as set forth in claim 2 wherein said sequentially pooled drops serially comprise Fractions OCA, OCB, OCC and OCD.

4. The method as set forth in claim 1 wherein said incubation step resulting in said incubation mixture comprises the steps of binding said antibody to Sepharose 4B in an affinity column and adding said extract of cells to said column.

5. The method as set forth in claim 4 wherein said antibody is antibody 701 which is a gamma globulin fraction isolated from female white New Zealand rabbits which have been injected with a perchloric extract of a precipitate formed between an antibody to Fraction OCA and normal human serum, normal ovarian tissue, normal long tissue and adenocarcinoma of the colon.

6. The method as set forth in claim 1 wherein said separation step comprises the step of collecting the unbound antigen from the incubation mixture.

7. The method of isolation of and purification of an antigen, NB/70K which is specific for ovarian carcinomas, which comprises the steps of isolating an extract of cells from an ovarian tumor, which contain a Fraction OCA, OCB, OCC or OCD, and separating the tumor specific antigen NB/70K therefrom.

8. The method as set forth in claim 7 wherein isolation of said extract of cells comprises the steps of making a perchloric extract of homogenized ovarian carcinoma cells, passing said extract through a concanavalin A:Sepharose 4B column, eluting said extract from said column, passing said eluted extract through a column containing anti-normal female serum, anti-normal ovarian tissue and anti-normal serum subfraction antibodies coupled to Sepharose 4B, passing the unbound extract therefrom through a Sephadex G-100 column and collecting the extract therefrom in 1 ml amounts as sequentially pooled drops.

9. The method as set forth in claim 8 wherein said sequentially pooled drops serially comprise Fractions OCA, OCB, OCC and OCD.

10. The method as set forth in claim 8 wherein said separation step comprises the steps of applying said extract of cells, in a Tris buffer to which Bromphenol blue and sucrose are added, to a 3% stacking gel and a 9% or 6% separating gel, electrophoresing said extract until the Bromphenol blue is 1 cm from the end of said gels, cutting said gels into horizontal strips and serially eluting said antigen in PBS.

11. The method of preparing anti-NB/70K from female New Zealand white rabbits which comprises the steps of withdrawing the blood of the rabbits a sufficient time after they had been immunized subcutaneously with NB/70K in Freunds' complete adjuvant for the rabbits immune system to generate the antibody to NB/70K, and isolating the gamma globulin containing anti-NB/70K from the blood by two precipitations with saturated ammonium sulfate.

12. The antibody, anti-NB/70K, which has been isolated in the gamma globulin by the method as set forth in claim 11.

13. A radioimmunoassay to detect the presence of an ovarian tumor specific antigen, NB/70K, and the amount of NB/70K present comprising the steps of isolating an extract of cells from an ovarian carcinoma, which contain a Fraction OCC, or OCA, or OCB, or OCD, adding said extract, containing known or unknown amounts of said antigen, and PBS to a container, adding anti-NB/70K in PBS to the container, allowing sufficient time for the anti-NB/70K to react with said extract, adding a radioiodinated extract of cells from an ovarian carcinoma, which contain a Fraction OCC, or OCA, or OCB, or OCD to the container after said time has expired, allowing sufficient time for the radioiodinated extract to react with the anti-NB/70K—extract adding Staphylococcus aureus of the Cowan I strain bearing protein A to the container, centrifuging the container, decanting the supernatant and counting the radioactivity of the resulting pellet.

14. The radioimmunoassay as set forth in claim 15 wherein the presence and amount of NB/70K in said unknown extract pellet is determined by comparing the radioactivity of said unknown extract pellet with the radioactivity of said pellets containing known amounts of NB/70K.

15. An improved radioimmunoassay, the Triton NB/70K assay, to detect the presence of an ovarian tumor specific antigen, NB/70K, and the amount of NB/70K present, comprising the steps of isolating Fraction OCC, or OCA, or OCB, or OCD, NB/70K, or isolating serum, adding said isolate, containing known or unknown amounts of said antigen, and PBS to a container, adding anti-NB/70K, in a Triton-EDTA buffer, to said container, allowing sufficient time for anti-NB/70K to react with said isolate, after said time has expired adding a radioiodinated NB/70K to said container, allowing sufficient time for said radioiodinated NB/70K to react with a complex of said anti-NB/70K and isolate, adding a 5% (w/v) Staphylococcus aureus of the Cowan I strain bearing protein A, in Triton-EDTA, solution to said container, centrifuging the container, decanting the supernatant and counting the radioactivity of the resulting pellet.

16. The radioimmunoassay as set forth in claim 15 wherein NB/70K is iodinated by the chloramine T method and labeled NB/70K is separated from unbound $I^{125}$ by dialysis against PBS.

17. The radioimmunoassay as set forth in claim 15 wherein serum is isolated from blood samples taken from individuals.

18. The assay as set forth in claim 15 wherein the step of testing for the presence and amount of NB/70K is carried out by determining the radioactivity of a pellet by comparison with the radioactivity of pellets containing known amounts of NB/70K.

* * * * *